United States Patent [19]

Hoover et al.

[11] Patent Number: 4,713,236
[45] Date of Patent: Dec. 15, 1987

[54] POLYMERIC AMINE CONDITIONING ADDITIVES FOR HAIR CARE PRODUCTS

[75] Inventors: M. Fred Hoover; Lawrence J. Guilbault, both of Topsfield, Mass.

[73] Assignee: Morton Thiokol, Inc., Chicago, Ill.

[21] Appl. No.: 327,670

[22] Filed: Dec. 7, 1981

[51] Int. Cl.$^4$ .................. A61K 7/06; C08F 124/00
[52] U.S. Cl. ........................ 424/70; 526/271; 526/310
[58] Field of Search ............ 424/70; 528/325; 526/310, 287, 320, 330, 331, 271; 525/60; 427/70

[56] References Cited

U.S. PATENT DOCUMENTS

| | | | |
|---|---|---|---|
| 3,488,307 | 1/1970 | Walus et al. | 526/310 X |
| 3,715,336 | 2/1973 | Nowak et al. | 526/310 |
| 3,862,306 | 1/1975 | Block et al. | 424/47 |
| 3,862,310 | 1/1975 | Quasius | 424/47 |
| 3,934,595 | 1/1976 | Dermain | 424/47 |
| 3,946,749 | 3/1976 | Papantoniou | 424/47 |
| 4,012,501 | 3/1977 | Farber | 424/DIG. 1 |
| 4,048,301 | 9/1977 | Papantoniou | 424/70 |
| 4,070,530 | 1/1978 | Hobbs | 525/60 |
| 4,198,495 | 4/1980 | Sekmakas et al. | 526/310 |
| 4,238,579 | 12/1980 | Leonard, Jr. et al. | 526/310 |
| 4,272,511 | 6/1981 | Papantoniou | 424/47 |
| 4,282,203 | 8/1981 | Jacquet et al. | 424/47 |
| 4,311,799 | 1/1982 | Miyake et al. | 526/310 |
| 4,324,780 | 4/1982 | Jacquet et al. | 424/47 |
| 4,348,380 | 9/1982 | Jacquet et al. | 424/70 |

Primary Examiner—Dale R. Ore
Attorney, Agent, or Firm—Gerald K. White

[57] ABSTRACT

Polymers containing the primary pendant amine group or the corresponding amine salt are useful for imparting good conditioning properties to hair.

12 Claims, No Drawings

POLYMERIC AMINE CONDITIONING ADDITIVES FOR HAIR CARE PRODUCTS

BACKGROUND OF THE INVENTION

Cationic quaternary ammonium compounds, both mono- and di-functional low molecular weight quaternary ammonium salts and high molecular weight polymers, are commonly employed as conditioning additives in hair care products such as shampoos, conditioners, creme rinses and setting gels to impart wet and dry combability, improve feel, enhance curl retention and impart antistatic properties to hair. The Cosmetics, Toiletries and Fragrances Association (CTFA) has established a designation index for quaternary ammonium compounds employed in cosmetic and toiletry products. Two low molecular weight quaternary ammonium compounds that are commonly used in haircare products because of their low cost are stearylbenzyldimethylammonium chloride (CTFA designation—stearalkonium chloride) and cetyltrimethylammonium chloride (CTFA designation—cetrimonium chloride).

High molecular weight cationic quaternary ammonium polymers (polyquats) are being increasingly used in hair care products because of their reported advantages over the simple quaternary ammonium salts in enhancing wet combability, mending split ends and improving appearance. Commonly used polyquats include: Polymer JR (CTFA designation—Quaternium 19) from Union Carbide, a quaternized cellulose; Gafquat (CTFA designation—Quaternium 23) from GAF Corp., a quaternized copolymer of vinylpyrrolidone and dimethylaminoethylmethacrylate; and Merquat 100 (Quaternium 40) from Merck, a homopolymer of dimethyldiallylammonium chloride.

These quaternary ammonium conditioning additives have in common the quaternary ammonium functional group:

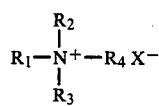

Where $R_1$ through $R_4$ may be various substituted or unsubstituted alkyl or aryl substituents, or in the case of the polyquats, represent alkylene or arylene segments of a polymer chain. Associated with the positively charged quaternary ammonium nitrogen atom is a negatively charged counterion. This anion, $X^-$ may be a halide, hydroxide, methylsulfate or similar negatively charged group. The tetravalent bonding on the nitrogen atom in quaternary ammonium compounds imparts a formal positive charge which is maintained across a broad pH range. Quaternary ammonium compounds with hydroxide anions are classified as strong bases.

This fundamental property of quaternary ammonium compounds undoubtedly contributes to the high degree of substantivity of cationic polyquats to the electronegative surface of hair. However, this substantivity can lead to a buildup of cationic polymer on the hair during repeated use which imparts a greasy feeling and tends to attract negatively charged dust particles from the air, leading to increased soiling rates. A further disadvantage to quaternary ammonium polymers as conditioning additives in hair care products is their incompatability with the anionic surfactants and soaps commonly used in these products. These anionic compounds are usually strong acid sulfonates and tend to form insoluble complexes with the cationic quaternary ammonium compounds. This undesirable reaction often leads to the formation of a precipitate during manufacture or poor product stability during storage. We have discovered that polymers containing primary pendant amine groups of the structure:

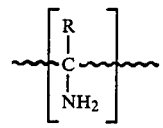

where:

〰 represents an organic polymer chain; and
R may be H, alkyl, aryl, —COOH, —COOR″, —CONH$_2$, etc.

or their corresponding ammonium salts are useful in overcoming the above discussed disadvantages.

SUMMARY OF THE INVENTION

The invention generally involves the use of the polymer of the invention for imparting good conditioning properties to hair when incorporated into hair care products such as shampoos, conditioners, creme rinses, setting gels, etc. Properties such as wet and dry combability, feel, and curl retention are enhanced. Antistatic properties are also imparted to the hair.

The polymer of the invention is made from ethylenically unsaturated addition polymerizable monomers and containing units of a pendant primary amino group of the following structure (Structure I):

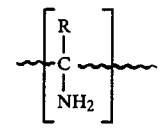

where:

〰 =an organic polymer chain;
R=H, alkyl, aryl, —COOH, —COOR″, or —CONH$_2$, etc, and
R″=methyl, ethyl or other lower alkyl;
or of an ammonium salt of said amino group having the following structure (Structure II):

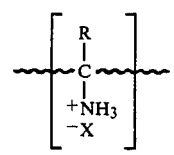

where:

〰 =an organic polymer chain,
R=H, alkyl, aryl, —COOH, —COOR″, or —CONH$_2$, etc. and
R″=methyl, ethyl, or other lower alkyl, and
$^-X$=halide, hydroxide, methyl sulfate, or similar negatively charged group;
or, admixture of the amino group and salt.

DETAILED DESCRIPTION OF THE INVENTION

It has been discovered that polymers containing pendant primary amino groups (structure I), or their corresponding ammonium salts (structure II) exhibit excellent properties as conditioning additives for hair-care products and overcome the disadvantages inherent to the quaternary ammonium polymers. Unlike the quaternary ammonium compounds, ionization of the polymeric amines of our invention is pH dependent. That is, at any pH there exists an equilibrium between the unionized (neutral charge) amine and the ionized (cationic or positive charge) ammonium form:

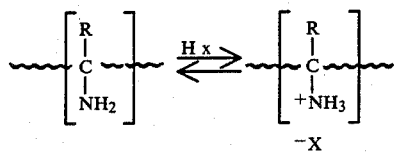

The ratio of ammonium to free base amine increases with decreasing pH and is dependent upon the basicity constant ($K_b$) of the specific amine. This basicity constant can be loosely defined as the pH at which the equilibrium concentrations of the ammonium and amine groups are equivalent.

Whereas, quaternary ammonium compounds behave as strong bases, the primary amine polymers of the present invention behave as weak bases. This significant distinction has important ramifications when polymeric materials containing these functional groups are employed as conditioning additives in hair-care products.

The polymeric amines of this invention exhibit sufficient cationic character in the pH range normally encountered with hair-care products (eg. pH 5-8) to impart excellent wet and dry combability, feel, manageability, antistatic and curl retention properties. Furthermore, the weak base behavior and presence of an equilibrium concentration of unionized amine groups tends to moderate the cationic charge intensity, thereby avoiding the undesirable properties of quaternary ammonium polymers, vis. tendency to buildup on the hair during repeated use, and insoluble complex formation with the anionic surfactants employed in hair-care products.

The invention encompasses homopolymers, copolymers and segmented (block and graft) copolymers containing pendant primary amine groups of structure I and their corresponding ammonium salts of structure II where $-X$ may be an anion such as halide, methylsulfate, hydroxide, etc., and R may be H, alkyl, aryl, —COOH, —COOR", —CONH$_2$ etc. This functional group is most commonly encountered in polymers containing the ethyleneamine mer unit, where R=H:

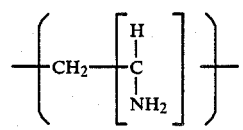

It is well-known that polymers containing this mer unit cannot be prepared directly from the corresponding monomer vinylamine. This compound is thermodynamically unstable and cannot be isolated since it isomerizes to the cyclic ethyleneimine:

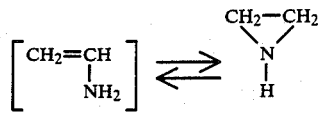

However, polymers containing the ethyleneamine mer unit can be prepared by conducting chemical transformations of suitable functional groups on preformed polymers. Several of these socalled "polymer analogous reactions" to prepare the parent homopolymer, poly(vinylamine) ie., poly(ethylene amine) have been reported, some of which are described in *Encyclop. Polym. Sci.*, Vol. 14, pg. 251.

The most common techniques to prepare polymers containing primary amine groups of Structure I in ethyleneamine mer units are:

1. Hydrolysis of a poly(N-vinylamide or imide) prepared from monomers such as N-vinyl formamide, N-vinylacetamide, N-vinylsuccinimide, N-vinyl phthalimide etc:

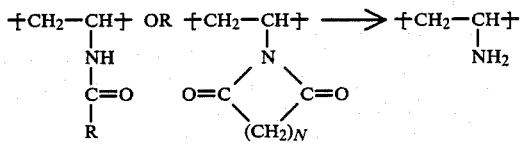

2. Hydrolysis of Poly(N-Vinyl carbamates):

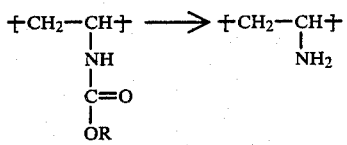

3. A variety of reactions (Curtius, Schmidt, Lossen, Hofmann) on polyacrylic acids, amides, aminimides or acid chlorides involving formation of an intermediate polyisocyanates or direct hydrolysis of a poly(alkenyl isocyanate) to generate pendant primary amino groups of Structure I:

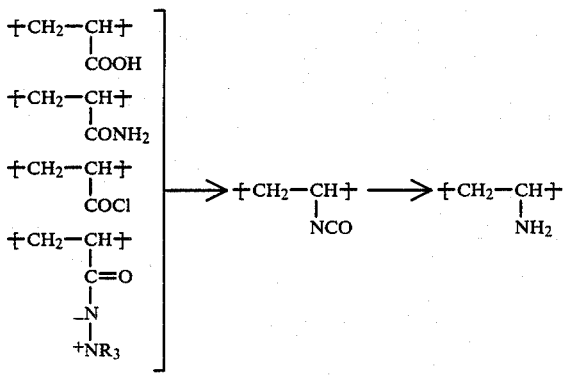

or,

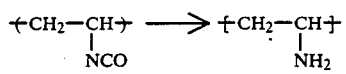

Alternative routes to introduce primary amine groups of Structure I into polymers are also known that do not involve vinylamine chemistry. For example, copolymers of carbon monoxide and olefins can undergo reductive amination to generate the desired primary amino group.

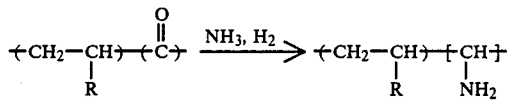

The polymers of our invention may be prepared by any of these methods to introduce the primary amino group. We have found the process involving hydrolysis of polymers based on N-vinylamides to be most convenient and versatile. Thus, a wide variety of homopolymers, copolymers and segmented (block and graft) polymers may be prepared by polymerizing a suitable N-vinylamide and optionally, other comonomers, using common polymerization processes. The resulting polymers can then be hydrolyzed to form the pendant primary ammonium groups and from this the corresponding pendant primary amine.

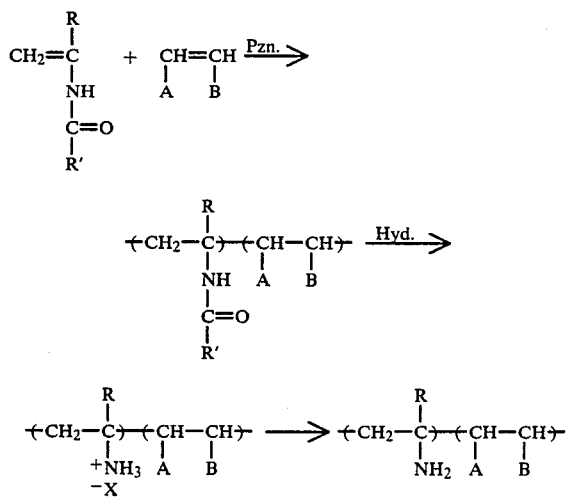

We have found N-vinyl acetamide (R'=CH₃) to be a convenient N-vinyl amide to use in preparing polymers containing the pendant primary amino group of Structure I where R=H. The monomer α-acetamidoacrylic acid can be employed to prepare polymers containing this amino group where R=—COOH.

Suitable comonomers may be selected from a wide variety of olefinic, vinylic or acrylic monomers to introduce other functional groups, if desired, into the amino polymers.

The "B" substituent on the comonomer mer unit may be H, alkyl, aryl, —COOH, —CONH₂, —COOR', hydroxyl etc. The "A" substituent is usually hydrogen, but may be other groups, such as —COOH for example when maleic anhydride is employed as comonomer.

These additional functional groups from the comonomer often enhance specific properties of the polymeric amines in their end use applications. We have found the following comonomers to be particularly useful:
vinyl sulfonate
vinylacetate
acrylic acid
acrylamide
2-acrylamido-2-methyl propane sulfonic acid
maleic anhydride Comonomers containing functional groups that are reactive under the hydrolysis conditions employed to generate the amino group can also be transformed during this process. Thus, a copolymer containing pendant hydroxyl groups and amino groups can be prepared by hydrolysis of a vinylacetate/N-vinylacetamide copolymer. Additional compositional modifications can be obtained by only partial hydrolysis of the pendant groups which serve as precursors of the amine functionality. Thus, partial hydrolysis of poly(N-vinylacetamide) would produce a copolymer containing both amine and acetamido functional groups.

The concentration of pendant primary amino groups of the Structure I in the hair care additive polymers of this invention may be varied over a wide range. The upper limit is defined by practical synthetic considerations and represented by polyvinylamine which contains one equivalent (1000 meq) of Structure I primary amine groups (R=H) per vinylamine mer unit (gram-molecular weight=43). Thus, the concentration of Structure I groups may be expressed as 1000/43=23.26 meq. Structure I amine groups/gram of polymer. Polymers containing much lower concentrations of the Structure I primary amino group are also effective. We have found that copolymers containing as little as 0.525 meq of Structure I amino groups/gram of polymer exhibit the desirable properties of the polymers of this invention.

The following examples describe the preparation, testing and performance of polymers containing pendant primary amino groups of Structure I as conditioning additives in hair-care products.

EXAMPLE 1

Preparation of Poly(vinylamine)

22.4 g N-vinyl acetamide (0.25 mole) is dissolved in 50 g deionized H₂O. The solution is added to a 300-ml 3-neck flask equipped with an overhead air-driven stirrer, a Bell condenser and a Graham condenser. 0.41 g AIBN (0.0025 mole) is added. After purging the system w/N₂, the system is closed to the atmosphere and a vacuum of 10 inches applied at the top of the Graham condenser. The solution is heated for 2 hours at 88° C., after which the pale yellow solution is cooled and diluted with 200 ml methanol.

The resulting poly(N-vinyl acetamide) is precipitated in 3.5 liters of acetone. The white polymeric product is washed with additional acetone and dried at 60° C. in vacuo. Hydrolysis of this polymer to form the hydrochloride salt of poly(vinylamine) is conducted by heating in 300 ml of 6N HCl at 85° C. for 12 hours under nitrogen. The poly(vinylamine) is isolated as the hydrochloride salt by addition of the hydrolysis solution to excess acetone with stirring. The product may be converted to poly(vinyl amine) by addition of sodium hydroxide to an aqueous polymer solution. The concentration of Structure I amine groups in the polymer was calculated to be 23.26 meq/g of polymer.

EXAMPLE 2

Preparation of 9:1 Mole Ratio Poly(Vinyl alcohol-co-vinylamine)

2.13 g N-vinyl acetamide (0.025 mole), 40.85 g vinyl acetate (0.475 mole) and 175 g deionized $H_2O$ are charged to a stirred 500 ml flask under a nitrogen purge. 0.62 g AIBN is dissolved in 10 ml hot methanol and is added to the monomers when the temperature of the solution has been raised to 38° C. The temperature is then raised to 80°–85° C. over the next hour and held there for 4 hours. As polymerization occurs, the product, a viscous white material, adheres to the stirrer. Following reaction, the solvent is poured off.

The polymer is then hydrolyzed in 300 ml of 6N HCl (1.8 m). The mixture is heated at 85° C. for 3 to 4 hours. As hydrolysis takes place, the polymer becomes soluble and darker in color. Following hydrolysis, the product is isolated as the hydrochloride salt by precipitation in acetone and is dried at 40° C. in vacuo. A beige to tan powder is obtained. Elemental analysis of the polymer indicated a 9:1 ratio of vinyl alcohol to vinylamine units and a calculated structure I amine content of 2.28 meq/gram.

EXAMPLE 3

Preparation of 1:2 Mole Ratio Poly(Acrylic Acid-co-vinylamine)

A 1000 ml, 4-neck resin kettle equipped with stirrer, $N_2$ purge thermocouple, and condenser is charged with 36 g acrylic acid (0.5 m), 85 g N-vinyl acetamide (1.0 m), 3.46 g $(NH_4)_2S_2O_8$ (0.015 m) and 686 ml $H_2O$. The temperature is raised to 80° C. and maintained for 3.5 hrs. After 2.5 hours, an additional 1.73 g $(NH_4)_2S_2O_8$ (0.007 m) is added. After cooling 20 g NaOH (0.5 m) is added. Poly(vinylacetamide-(co)-sodium acrylate) is isolated by evaporating the water, redissolving in a minimum of MeOH, and precipitation into acetone. The product is a yellow solid. The polymer is redissolved in water and 250 ml of 37% HCl (2.5 m) added in a 500 ml round bottom flask equipped with a reflux condenser. Reflux is maintained for 20 hours. The product is a clear yellow solution of the polymer in the hydrochloride salt form. Elemental analysis of the polymer indicated a 1:2 ratio of acrylic acid to vinylamine units and a calculated Structure I amine content of 12.65 meq/gram.

EXAMPLE 4

Preparation of 9:1 Mole Ratio Poly(2-acrylamido-2-methyl propane sulfonic acid-co-vinylamine)

82.8 g 2-acrylamido-2-methyl propane sulfonic acid (0.4 m) dissolved in 200 ml deionized $H_2O$ is neutralized with 16 g NaOH (0.4 m) and charged to a 500 ml 4-neck resin kettle equipped with a stirrer, reflux condenser, thermocouple, and $N_2$ inlet. To this 3.8 g N-vinyl acetamide (0.045 m) dissolved in 58 ml $H_2O$ and 0.87 g AIBN (0.1 phm) dispersed in 30 ml $H_2O$ are added with stirring. The reaction mixture is purged with nitrogen and the temperature raised to 92° C. and maintained for 3 hours. After cooling, 124 g of the aqueous reaction product solution is charged to a 500 ml round bottom flask with condenser and 2.64 ml 37% aqueous HCl (0.0267 m) added. The solution is refluxed for 20 hours. The resulting product is a pale yellow-green liquid containing 10% polymer by weight, in the hydrochloride salt form. Elemental analysis of the isolated polymer indicated a 9:1 mole ratio of 2-acrylamido-2-methylpropane sulfonic acid to vinylamine groups and a calculated Structure I amine content of 0.53 meq/gram.

EXAMPLE 5

Preparation of 1:1 Mole Ratio Poly(vinyl alcohol-co-vinylamine)

A one liter flask fitted with stirrer, condenser, $N_2$ inlet and thermometer was charged with 93 gram vinyl acetate, 68 gram N-vinylacetamide and 160 g methanol. After flushing with nitrogen, 2.44 g of AIBN was added in three increments over two hours while refluxing (64° C.) the reaction for 5.5 hours. After cooling, the viscous solution was added to stirred acetone to precipitate the polymer as a white solid. Elemental analysis of the polymer indicated a 1:1 mole ratio of vinyl acetate to N-vinylacetamide units.

The polymer was hydrolyzed by dissolving 23 grams in 350 ml of water containing 14 g NaOH and heating for 24 hrs. at 95° C. The polymer precipitate was dissolved in water and reprecipitated into acetone. The calculated Structure I amine content of the hydrolyzed polymer was 11.49 meq/gram.

EXAMPLE 6

Preparation of a 3:1 Mole Ratio Poly(vinyl alcohol-co-vinylamine)

This polymer was prepared according to the procedure described in Example 8 using 138 grams vinyl acetate, 34 grams N-vinylacetamide, 180 grams methanol and 2.40 g AIBN. Elemental analysis of the polymer isolated by precipitation into ether indicated a 3:1 molar ratio of vinyl acetate to N-vinylacetamide.

The polymer was hydrolyzed to poly(vinylalcohol-co-vinyl amine) according to the procedure of Example 8. The calculated Structure I amine content was 5.71 meq/gram.

EXAMPLE 7

Poly(Vinyl Sulfonate-co-vinylamine)

A sample of this polymer was obtained from Polysciences Inc., in the sodium salt form. Based on the reported comonomer ratio of 3:2, vinyl sulfonate to vinylamine, the Structure I amine content of the polymer is calculated as 4.88 meq/gram.

EXAMPLE 8

Preparation of 2:3 Mole Ratio Poly(Maleic acid-co-vinylamine)

A five hundred ml flask fitted with stirrer, condenser, $N_2$ inlet and thermometer was charged with 49 grams maleic anhydride, 42.5 grams N-vinylacetamide and 150 ml THF. After purging with $N_2$, 1.64 grams AIBN was added and the contents heated at 70° C. for four hours. Additional AIBN, 0.82 g was added and after two more hours at 70° C., the contents were cooled and precipitated into ether. Characterization of the isolated polymer by potentiometric titration and by elemental analysis indicated a 2:3 mole ratio of maleic anhydride to N-vinyl acetamide units.

The polymer was hydrolyzed by dissolving 60 grams in 100 ml water containing 150 g 37% HcL. The solution was heated at reflux (107°–109° C.) for four hours under $N_2$ and after sitting overnight, the solution was evaporated down to 150 ml volume and added to stirred acetone. Elemental and infrared analysis of the maleic acid-vinylamine copolymer indicated a calculated Structure I amine content of 13.33 meq/gram.

EXAMPLE 9

Preparation of 1:1 Mole Ratio Poly(Acrylic Acid-co-vinylamine)

A 500 ml flask fitted with stirrer, condenser, $N_2$ inlet and thermometer was charged with 31.88 g N-vinyl acetamide, 27.0 g acrylic acid, 334.5 ml distilled water and 2.60 g ammonium persulfate. The contents were purged with $N_2$ and heated for 3.5 hours at 70°-80° C. After cooling, the water was evaporated and the solids, dissolved in methanol, were precipitated into ether. The polymer, 70 grams, was dissolved in 148 ml of 37% HCl and refluxed overnight to affect hydrolysis. The Structure I amine content of the copolymer, based on the 1:1 monomer feed ratio was calculated as 8.69 meq/gram.

EXAMPLE 10

Preparation of 9:1 Mole Ratio Poly(vinylamine-co-2-acrylamido-2-methylpropane sulfonic acid)

A 250 ml flask fitted with stirrer, condenser, $N_2$ inlet and thermometer was charged with 18.63 grams 2-acrylamido-2-methylpropane sulfonic acid, 68 grams N-vinylacetamide, 4 g NaOH, 168 ml water and 0.87 grams AIBN dissolved in 20 ml ethyl acetate. The contents were heated at 92° C. for 3 hours and then cooled. Hydrolysis was affected by adding 43.4 ml 37% HCl and heating for 20 hours at 90° C. The calculated Structure I amine content of the copolymer based on monomer feed ratios is 15.15 meq/gram.

EXAMPLE 11

Preparation of Poly(Alpha-amino acrylic acid)

2-Acetamidoacrylic acid (30 g) and azobisisobutyronitrile (1.9 g) are dissolved in N,N-dimethylformamide (130 ml) in a 250 ml round bottom flask. The flask, sealed with a syringe cap, is purged with $N_2$ for one hour. The monomer is polymerized at 60° C. over a 20-hour period. The viscous solution is added to ten times its volume of cold acetone. The precipitated polymer is filtered by suction and dried under vacuum overnight at room temperature to give poly(2-acetamidoacrylic acid) in quantitative yield, $\eta_{sp}$(1 g/dl,DMF)=0.37 dl/g at 25°.

The hydrolysis of poly-2-acetamidoacrylic acid) is accomplished by heating the polymer in 3N HCl. The polymer (25 g) is dissolved in water (500 ml) in 1 liter 3 neck round bottom flask equipped with a mechanical stirrer, condenser and a gas inlet tube. Con. HCl (165 ml) is slowly added to the water solution of polymer. The system is purged with $N_2$ and then heated to reflux and maintained at this temperature for about 12 hours. Poly(alpha-aminoacrylic acid), which precipitates during the course of hydrolysis, is collected by suction filtration, after the reaction mixture has cooled to room temperature, and washed with acetone. The dried polymer, a white powder, amounts to 11 g (57.4% yield). The concentration of Structure I amine groups was calculated to be 11.49 maq/g of polymer.

Each amino-containing polymer was evaluated as a hair-conditioning additive with respect to effect on overall manageability (eg., wet combability, dry combability and feel) and curl retention. Details of the test are described below:

Each polymer was evaluated sequentially for wet and dry combability and feel in model conditioner and shampoo/conditioner. Performance was evaluated by several independent observers on coded samples, rating the treated hair as "good" or "poor" within a given test series.

A separate 2 gram hair swatch was used for each polymer. The 8" virgin dark brown hair was obtained from DeMeo Brothers, 49 W. 28th Street, New York, NY 10001. The swatch was immersed in the model formulation solution for 1 minute, rinsed with running tap water for 5 seconds, and dunked 10 times in distilled water. The swatch was subsequently evaluated as follows:

1. Combability—Wet: The swatch was combed wet and rated for ease of combing.
2. Combability—Dry: After wet combing the swatch was air dried, combed and rated again for ease of combing.
3. Feel: After dry combing, each swatch was evaluated for feel by two (2) people and rated.

The above test sequence was repeated four (4) times on the swatch for each material tested. The % manageability was calculated by subtracting the number of "poor" observations from the number of "good" observations and dividing by the total number of observations.

The treated hair swatches were also evaluated for curl retention as shown below following completion of comb and feel testing.

The dry swatch was dipped in water, curled wet on ½" diameter rollers and air dried. It was then placed in a humdiity chamber wet at 85% RH, 72° F. The curler was removed upon placement in the chamber. After 1 hour exposure, the length of the hair swatch was measured and curl retention calculated using the equation below, or in some cases rated as "good", "poor", "average" or "none".

$$\% \text{ Curl Retention:} \frac{\text{(Initial Length } - \text{ Uncurled Length)}}{\text{(Initial Length } - \text{ Curled Length)}} \times 100$$

It should be mentioned that all test methods are subject to human appraisal and thus should be considered to give subjective results although every effort was made to insure unbiased opinions. The data are qualitative rather than quantitative.

The results of the testing are set forth in Tables I and II. As may be observed, the addition of the polymer of the invention to hair conditioning products leads to the attainment of generally good wet and dry combability and curl retention.

A concentration range of from about 0.1 to 10 wt% of the polymer of the invention has been found to be useful in hair conditioning shampoos and the like. A concentration on the order of about 0.5 wt % is preferred. For other types of hair care formulations, the amount required will vary depending upon the type of treatment and quality of the hair.

TABLE I

HAIR-CARE ADDITIVE PERFORMANCE IN MODEL CONDITIONER FORMULATION*

| Polymer of Example No. | Conc. of Structure I Amine Units (meq/g) | Percent Manageability | Percent Curl Retention |
|---|---|---|---|
| 1 | 23.26 | 13 | Good |
| 2 | 2.28 | 60 | Good |
| 3 | 12.65 | N.T. | N.T. |

TABLE I-continued
HAIR-CARE ADDITIVE PERFORMANCE IN MODEL CONDITIONER FORMULATION*

| Polymer of Example No. | Conc. of Structure I Amine Units (meq/g) | Percent Manageability | Percent Curl Retention |
|---|---|---|---|
| 4 | 0.53 | 63 | 37 |
| 5 | 11.49 | 67 | Avg. |
| 6 | 5.71 | 60 | Avg. |
| 7 | 4.88 | 38 | None |
| 8 | 13.33 | N.T. | N.T. |
| 9 | 8.69 | N.T. | N.T. |
| 10 | 15.15 | 56 | 22 |
| 11 | 11.49 | N.T. | N.T. |

*Hair Conditioner: 0.5% polymeric additive in distilled water
N.T. = Not Tested
Avg. = Average Performance

TABLE II
HAIR CARE ADDITIVE PERFORMANCE IN MODEL CONDITIONING SHAMPOO FORMULATION*

| Polymer of Example No. | Conc. of Structure I Amine Units (meq/g) | Percent Manageability | Percent Curl Retention |
|---|---|---|---|
| 1 | 23.26 | 67 | Good |
| 2 | 2.28 | 56 | 21 |
| 3 | 12.65 | 40 | None |
| 4 | 0.53 | 63 | 22 |
| 5 | 11.49 | 27 | Poor |
| 6 | 5.71 | 67 | Avg. |
| 7 | 4.88 | 87 | Avg. |
| 8 | 13.33 | 80 | N.T. |
| 9 | 8.69 | 47 | None |
| 10 | 15.15 | 56 | 21 |
| 11 | 11.49 | 80 | N.T. |

*Conditioning Shampoo: 2.0% polymeric additive in 12.5% ammonium lauryl sulfate solution (distilled water)
N.T. = Not Tested
Avg. = Average Performance

We claim:

1. A hair conditioning product which is a member selected from the group consisting of shampoos, conditioners, creme rinses, and setting gels and containing an effective amount of a polymer for imparting good conditioning properties to hair made from ethylenically unsaturated addition polymerizable monomers and containing units of a member selected from the group consisting of a pendant primary amino group of the following structure:

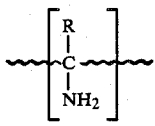

where:

~~~ = an organic polymer chain;
R = H, alkyl, aryl, —COOH, —COOR" or —CONH$_2$, and
R"— methyl, ethyl or other lower alkyl; an ammonium salt of said amine group of the following structure:

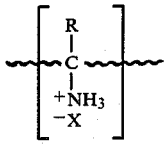

where:
~~~ = an organic polymer chain,
R = H, alkyl, aryl, —COOH, —COOR" or —CONH$_2$, and
R" = methyl, ethyl or other lower alkyl, and
$^-$X = halide, hydroxide, methyl sulfate, or similar negatively charged group;
or admixtures of the amino group and salt.

2. The hair conditioning product of claim 1, wherein: said polymer contains an amine unit in a concentration from about 0.5 to 25.0 meq/gram.

3. The hair conditioning product of claim 1 or 2, wherein: said polymer is polyvinylamine.

4. The hair conditioning product of claim 1 or 2, wherein: said polymer comprises a copolymer which contains vinylamine as a reoccuring unit.

5. The hair conditioning product of claim 4, wherein: said copolymer contains a conmonomer selected from the group consisting of vinyl alcohol, acrylic acid, acrylamide, maleic anhydride, vinyl sulfonate, and 2-acrylamido-2-methyl propane sulfonic acid.

6. The hair conditioning product of claim 5, wherein: said vinyl alcohol is a reoccuring unit.

7. The hair conditioning product of claim 6, wherein: vinyl alcohol and vinylamine are present in a ratio of from 9:1 to 1:9.

8. The hair conditioning product of claim 5, wherein, said comonomer is 2-acrylamido-2-methyl propane sulfonic acid.

9. The hair conditioning product of claim 8, wherein, 2-acrylamido-2-methyl propane sulfonic acid and vinylamine are present in a ratio of from 9:1 to 1:9.

10. The hair conditioning product of claim 1 or 2, wherein: said polymer is a homopolymer of poly(alpha-amino acrylic acid).

11. The hair conditioning product of claim 1 or 2, wherein: said polymer comprises a copolymer which contains alpha-amino acrylic acid as a comonomer.

12. A method of conditioning hair, comprising applying the product of claim 1, 2, 7, 9, or 11 to hair so as to obtain good hair conditioning properties.

* * * * *